United States Patent [19]

Herrmann et al.

[11] Patent Number: 4,477,661

[45] Date of Patent: Oct. 16, 1984

[54] PROCESS FOR THE PREPARATION OF 4-HYDROXY-3-(HETEROCYCLOCAR-BAMOYL)-2H-1,2-BENZOTHIAZINE-1,1-DIOXIDES

[75] Inventors: Wolfgang Herrmann, Merzhausen; Wolfram Geibel, Reute; Gerhard Satzinger, Denzlingen, all of Fed. Rep. of Germany

[73] Assignee: Warner-Lambert Company, Morris Plains, N.J.

[21] Appl. No.: 478,763

[22] Filed: Mar. 25, 1983

[30] Foreign Application Priority Data

Apr. 3, 1982 [DE] Fed. Rep. of Germany ....... 3212485

[51] Int. Cl.$^3$ .................. C07D 401/12; C07D 417/12
[52] U.S. Cl. ..................................... 544/49
[58] Field of Search ........................ 544/49

[56] References Cited

U.S. PATENT DOCUMENTS

| | | | |
|---|---|---|---|
| 3,501,466 | 3/1970 | Rasmussen | 544/49 |
| 3,770,733 | 11/1973 | Sianesi et al. | 544/49 |
| 3,822,258 | 7/1974 | Zinnes et al. | 544/49 |
| 4,116,964 | 9/1978 | Zinnes et al. | 544/49 |
| 4,376,119 | 3/1983 | Ozaki et al. | 544/49 |

*Primary Examiner*—John M. Ford
*Attorney, Agent, or Firm*—Ronald A. Daignault

[57] ABSTRACT

The present invention provides a process for the preparation of 4-hydroxy-3-(heterocyclocarbamoyl)-2H-1,2-benzothiazine-1,1-dioxides of the general formula:

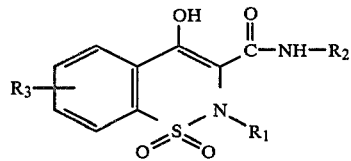

wherein $R_1$ is a hydrogen atom or a methyl radical, $R_2$ is a nitrogen-containing heterocyclic radical and $R_3$ is a hydrogen or halogen atom or a methyl radical, and of the alkali metal, alkaline earth metal and amine salts thereof, by the reaction of an amine-substituted, nitrogen-containing heterocyclic compound with a haloacetyl halide, reaction of the intermediate thus obtained with sodium benzoic acid sulphimide, ring expansion of the benzoisothiazole ring to give a benzothiazine ring and, in case $R_2$ is to be an isoxazolyl radical, reverse rearrangement of the oxadiazole-ring formed by ring expansion to the isoxazolyl ring, wherein (in a one-pot reaction A) the reaction of an amine-substituted, nitrogen-containing heterocyclic compound with a haloacetyl halide is carried out, without the addition of a base, in boiling ethyl acetate, the intermediate formed is, without isolation, reacted with sodium benzoic acid sulphimide and the reaction product isolated, whereafter, in a one-pot reaction B, the reaction product from the one-pot reaction A is reacted in a dipolar aprotonic solvent under an atmosphere of a protection gas with a strongly basic alkali-alkohole and thereafter with so much acid that about 2 equivalents of base remained unneutralized in the reaction solution and, if desired, the benzothiazine ring is N-methylated in the usual manner and the product obtained is, if desired, converted in known manner into an alkali metal, alkaline earth metal or amine salt.

9 Claims, No Drawings

PROCESS FOR THE PREPARATION OF 4-HYDROXY-3-(HETEROCYCLOCARBAMOYL)-2H-1,2-BENZOTHIAZINE-1,1-DIOXIDES

The present invention is concerned with a process for the preparation of 4-hydroxy-3-(heterocyclocarbamoyl)-2H-1,2-benzothiazine-1,1-dioxides.

Federal Republic of Germany Patent Specification No. 22 08 351 describes a process for the preparation of 4-hydroxy-3-(isoxazolocarbamoyl)-2H-1,2-benzothiazine-1,1-dioxides of the general formula:

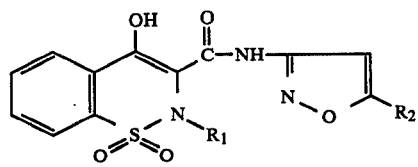

wherein $R_1$ is a hydrogen atom or a methyl radical and $R_2$ is a hydrogen atom or a methyl radical, and of the alkali metal, alkaline earth metal and amine salts thereof. The compounds prepared by this known process possess anti-rheumatic properties.

The known process of preparation proceeds, for example, in the case of a compound of the above-given general formula in which $R_1$ and $R_2$ are both methyl radicals, in four separate reaction steps with a total yield of 40 to 45%:

Step 1.

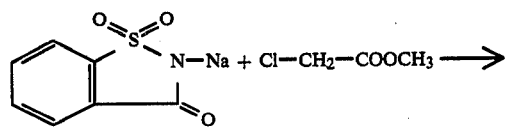

Step 2.

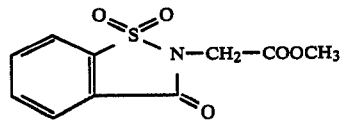

(II)

Step 3.

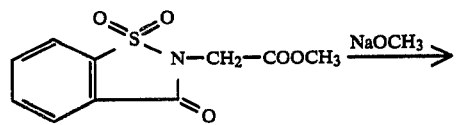

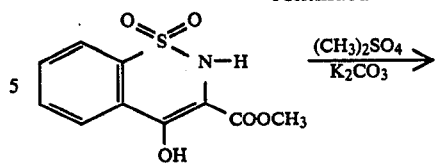

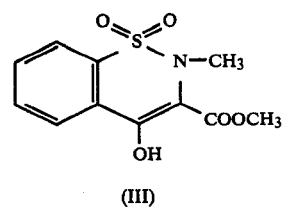

(III)

Step 4.

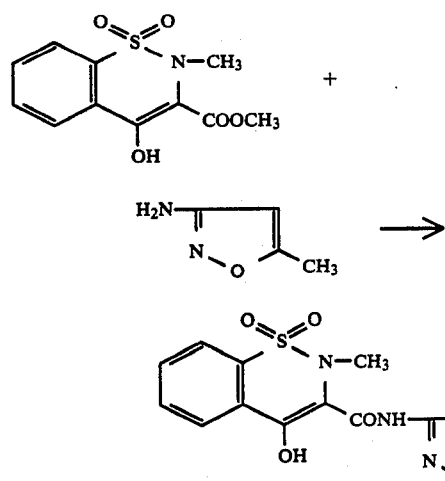

4-hydroxy-3-(5-methyl-3-isoxazolylcarbamoyl)-2-methyl-2H—1,2-benzothiazine-1,1-dioxide In the case of another process known from U.S. Pat. Spec. No. 4,041,042, the preparation of the compounds in question takes place by the following reaction sequence in five steps, each intermediate being isolated and further worked up in the following step:

Step I.

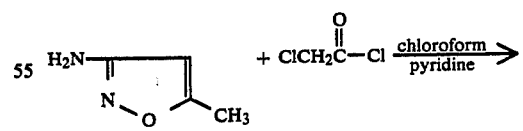

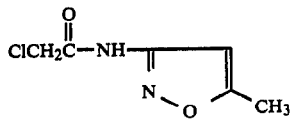

I

Step II

3
-continued

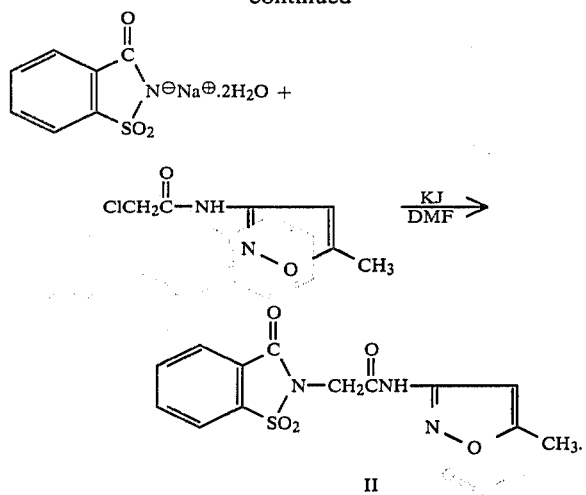

Step III

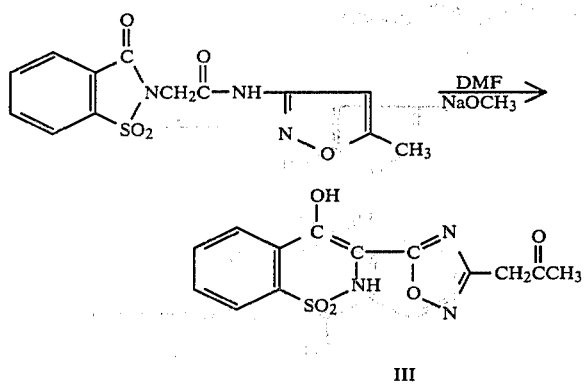

Step IV

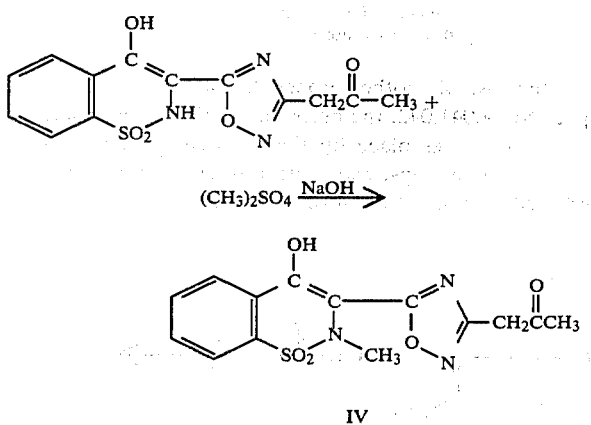

Step V

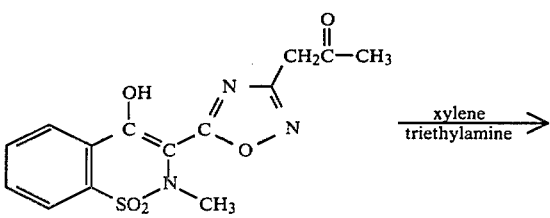

-continued

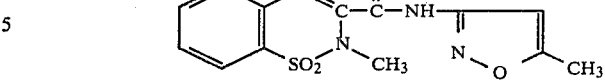

V

Disadvantages of the process known from this U.S. Pat. Spec. No. 4,041,042 include the following:
1. it proceeds via five steps, with isolation of the intermediates, for which reason a relatively large expenditure of work, energy and time is necessary;
2. the total yield is only 27%;
3. the intermediate (I), i.e. the reaction product of 3-amino-5-methylisoxazole and chloroacetyl chloride, is a strong skin irritant.

It is an object of the present invention to provide a process for the preparation of 4-hydroxy-3-(heterocyclocarbamoyl)-2H-1,2-benzothiazine-1,1-dioxides which, with a lesser expenditure of work, energy and time, gives higher yields, can be carried out on a large scale and fully takes into account the hygienic aspects during working.

Thus, according to the present invention, there is provided a process for the preparation of 4-hydroxy-3-(heterocyclocarbamoyl)-2H-1,2-benzothiazine-1,1-dioxides of the general formula:

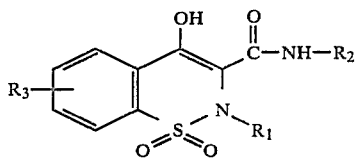

wherein $R_1$ is a hydrogen atom or a methyl radical, $R_2$ is a nitrogen-containing heterocyclic radical and $R_3$ is a hydrogen or halogen atom or a methyl radical, and of the alkali metal, alkaline earth metal and amine salts thereof, by the reaction of an amine-substituted, nitrogen-containing heterocyclic with a haloacetyl halide, reaction of the intermediate thus obtained with sodium benzoic acid sulphimide, ring expansion of the benzoisothiazole ring to give a benzothiazine ring and in case $R_2$ is to be an isoxazolyl-radical reverse rearrangement of the oxadiazole-ring formed by ring expansion to the isoxazolyl-ring, wherein, in a one-pot reaction A, the reaction of an amine-substituted, nitrogen-containing heterocyclic compound with a haloacetyl halide is carried out, without the addition of a base, in boiling ethyl acetate, the intermediate formed is, without isolation, reacted with sodium benzoic acid sulphimide and the reaction product isolated, whereafter, in a one-pot reaction B, the reaction product from the one-pot reaction A is reacted in a dipolar aprotonic solvent under an atmosphere of a protection gas with a strongly basic alkali-alkohole and thereafter with so much acid that about 2 equivalents of base remained unneutralised in the reaction solution and, if desired, the benzothiazine ring is N-methylated in the usual manner and the product obtained is, if desired, converted in known manner into an alkali metal, alkaline earth metal or amine salt.

Preferred examples of nitrogen-containing heterocyclic radicals $R_2$ include isoxazole, thiazole and pyridine radicals, which can also be substituted, e.g. by lower alkyl or alkoxy groups, especially methyl or methoxy groups.

The process according to the present invention makes possible a very simple and inexpensive process for the preparation of compounds of the given general formula. As mentioned, it consists of two successive one-pot reactions (referred to as one-pot reactions A and B) in which, in each case, two and three reaction steps, respectively, take place one after the other, without isolation of the intermediates. In step A the yield is 94% and in step B is 82 to 86%, which corresponds to a total yield of 77 to 80%, in comparison with a yield of 40 to 45% in the case of the process according to Federal Republic of Germany Patent Specification No. 22 08 351 and of 27% in the case of the process according to U.S. Patent Spec. No. 4,041,042.

The process according to the present invention is described in the following, using as an example the preparation of 4-hydroxy-3-(5-methyl-3-isoxazolylcarbamoyl)-2-methyl-2H-1,2-benzothiazine-1,1-dioxide (Isoxicam):

One-pot reaction A

Step 1

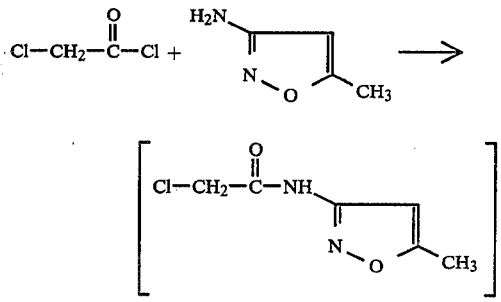

Step 2

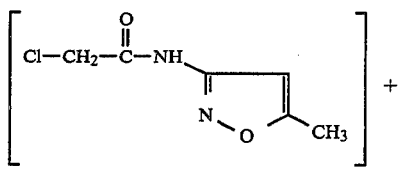

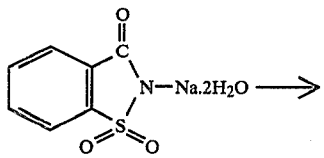

-continued

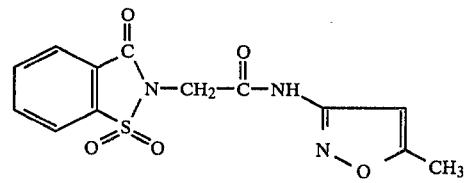

(2)

In a first reaction step, 3-amino-5-methylisoxazole is reacted with chloroacetyl chloride. This reaction is, in the case of the reaction known from U.S. Pat. Spec. No. 4,041,042, carried out in chloroform with the addition of pyridine to bind the hydrogen chloride formed. Pyridine hydrochloride thereby precipitates out of the solution, together with the reaction product, and has to be removed by repeated washing and slurrying in water.

Surprisingly, we have now found that this reaction can be carried out in boiling ethyl acetate without the addition of a base, the hydrogen chloride formed distilling off with some of the ethyl acetate and thus being removed from the reaction mixture. Actually, it was to have been assumed that the hydrogen chloride formed would be bound in a salt-like manner by unreacted aminoisoxazole and that this would, consequently, not be able to react with the acid chloride, which would have given rise to a poor yield or to the necessity of having to use the aminoisoxazole in excess. Due to the fact that a base does not have to be added for binding the hydrogen chloride and that the latter distils off practically completely, a salt-free reaction mixture is obtained which, again after distilling off the remaining ethyl acetate, makes possible the immediate further reaction with sodium benzoic sulphimide to give product (2). Thus, it is possible to avoid to isolate the skin-irritant intermediate (1). The complete reaction thereof is ensured by the use of an excess of sodium benzoic acid sulphimide. Product (1) can no longer be detected in product (2) so that it can be assumed that the further working up of product (2) will not result in harm to the skin.

The end product of the one-pot reaction A is then obtained by precipitation out with water in a yield of 90 to 95% and in a purity of 98 to 99%.

According to the process of the present invention, the dried reaction product from the one-pot reaction A is now converted in a one-pot reaction B in dimethylformamide as solvent, into 4-hydroxy-3-(5-methyl-3-isoxazolylcarbamoyl)-2-methyl-2H-1,2-benzothiazine-1,1-dioxide by the steps illustrated by the following equations:

One-pot reaction B

Step 3

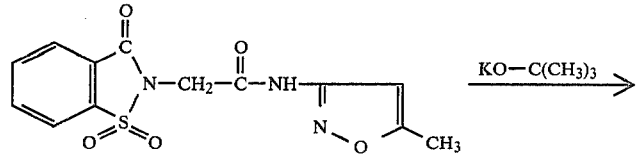

(2)

-continued

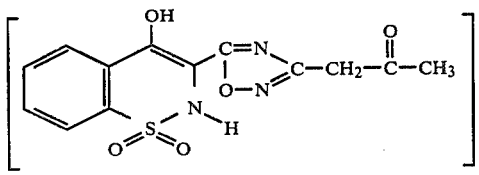

(2) (not isolated)

Step 4

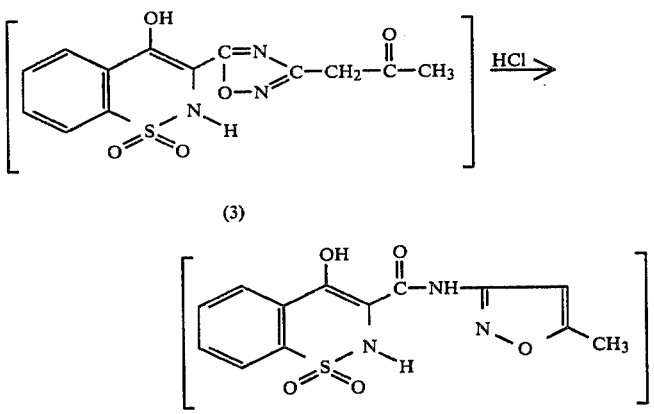

4-hydroxy-3-(5-methyl-3-isoxazolyl-
carbamoyl)-2-methyl-2H—1,2-
benzothiazine-1,1-dioxide (5)

According to the process known from Federal Republic of Germany patent specification No. 22 08 351, the rearrangement of the benzoisothiazole ring to the benzothiazine ring is achieved by the action of sodium methylate, the yield being 60%. We have now found that the ring expansion proceeds almost quantitatively when using a stronger basic alkali-alkoholate as base. As stronger basic alkali-alkoholate there are understood basic alkoholates exceeding sodium methylate in basicity, especially branched alkali-alkoholates such as potassium tert. butylate. As in the Case of the action of sodium methylate, simultaneously with the ring expansion, the isoxazole ring of the side chain is rearranged to give a 1,2,4-oxadiazole ring (3). This rearrangement must again be reversed in order to obtain 4-hydroxy-3-(5-methyl-3-isoxazolylcarbamoyl)-2-methyl-2H-1,2-benzothiazine-1,1-dioxide. According to the process known from U.S. Pat. Spec. No. 4,041,042, this takes place in the last reaction step by heating with triethylamine in xylene, after having methylated the nitrogen of the benzothiazine ring in the penultimate step. We have now found that this reversed rearrangement to give (4) in the scope of the process according to the present invention can, surprisingly, be achieved directly in the reaction solution containing the product (3) when a particular amount of an acid is added. This acid can be organic or inorganic. It is preferred to use hydrogen chloride, either in the form of a solution in a dipolar aprotonic solvent, preferably dimethylformamide or dimethylsulphoxide or as concentrated aqueous hydrochloric acid diluted with said dipolar aprotonic solvent. The amount of acid used should 2 equivalents of base, for example in the case of the use of 4 equivalents of tert.-butylate, 2 equivalents of acid are added, whereas in the case of the use of 3 equivalents of tert.-butylate only 1 equivalent of acid is added. The reaction temperature of the rapidly proceeding reversed rearrangement of product (3) to product (4) can be from −5 to +25° C. and is preferably about +5° C. The reaction is suitably carried out in an atmosphere of a protection gas e.g. nitrogen, argon or helium.

Subsequently, in the same solution, after the addition of 1 equivalent of potassium hydroxide, there can be carried out the N-methylation of product (4) to give product (5), using dimethyl sulphate. The end product is precipitated out by acidification and the addition of water. On a pilot scale, this one-pot reaction (3) to (4) to (5) can, without difficulty, be carried out in half a day.

The following Example is given for the purpose of illustrating the present invention:

EXAMPLE 1

One-pot reaction A

Reaction steps 1 and 2

27.75 liters of ethyl acetate are placed in a 100 liter Pfaudler kettle and 1850 g. (18.85 mole) 3-amino-5-methyl-isoxazole are introduced. The mixture is brought to the boil, with gentle stirring, whereby dissolution takes place. About 2 liters of ethyl acetate are distilled off in order to remove any traces of water possibly present in the solvent and in the kettle. Thereafter, a mixture of 1.5 liters (18.85 mole) chloroacetyl chloride in 4.5 liters ethyl acetate are allowed to run in in the course of about 1 hour. By gentle heating, the mixture is kept at the boil; the boiling point thereby decreases from its initial value of 77° C. to 72° C. During this running in, about 11 liters of ethyl acetate are distilled off. The hydrogen chloride formed by the reaction escapes from the reaction mixture and dissolves in the condensed ethyl acetate. After completion of the running in, the reaction mixture is further boiled for 1 hour in order completely to expel the hydrogen chloride from the reaction mixture, a further 12 liters of ethyl acetate thereby being distilled off. After discontinuing the heating, a solution of 5451 g. (22.6 mole) sodium benzoic acid sulphimide dihydrate and 312 g. (1.885 mole) potassium iodide in 18.85 liters dimethylformamide are allowed to run in in the course of about 5 minutes. Subsequently, the reaction mixture is heated to 90° C. and stirred at this temperature for 1.75 hours. After discontinuing the heating, 52 liters of water are allowed to run in quickly. The product which crystallises out from the initially clear solution is centrifuged off, washed with 20 liters of water in the centrifuge and dried at 50° C. to constant weight. Yield of product (2): 5.7 kg. (94% of theory); m.p. 217.6° C.; water content according to the Karl Fischer method; <0.1%; HPLC: content 98–99%; product (1) not detectable (<0.1%).

One-pot reaction B

Reaction steps 3, 4 and 5

13.5 liters of dimethylformamide are placed in a 100 liter Pfaudler kettle under an atmosphere of nitrogen and, while stirring gently, 4490 g. (40 mole) potassium tert.-butylate are introduced. With good stirring and cooling with cold water, a solution, prepared under an atmosphere of nitrogen, of 3213 g. (10 mole) of the reaction product (b 2) from one-pot reaction A in 11.2 liters dimethylformamide is allowed to run in in the course of 10 minutes at a temperature of about 25° C.

The reaction mixture is heated with steam to 50° C. and stirred for 15 minutes. Thereafter, it is cooled to 0° C. and a solution of 729 g. (20 mole) gaseous hydrogen chloride in 3.2 liters dimethylformamide allowed to run in in the course of about 15 minutes, while cooling with brine to a temperature of +5° C. After the addition of a solution of 660 g. (10 mole) 85% potassium hydroxide in 1.32 liters of water, 2522 g. (20 mole) dimethyl sulphate are allowed to run in in the course of about 10 minutes, with good stirring. The temperature thereby increases to 30° C. Thereafter, the reaction mixture is stirred for 30 minutes at 30° C. In order to destroy excess dimethyl sulphate, 1000 ml. (about 13.3 mole) concentrated aqueous ammonia solution are added thereto and the reaction mixture thereafter stirred for 30 minutes at 30° C. After the addition of 50 liters of water, a mixture of 3 liters (37.5 mole) concentrated hydrochloric acid in 20 liters of water is allowed to run in. The reaction mixture is cooled to 20° C. and the product is centrifuged off, washed with water and dried at 60° C. There are obtained 2.78 kg. (83% of theory) of crude 4-hydroxy-3-(5-methyl-3-isoxazolylcarbamoyl)-2-methyl-2H-1,2-benzothiazine-1,1-dioxide. The purity of the product, according to HPLC, is 96%; m.p. 253° C. (decomp.).

(EXAMPLE 1A)

Variation II 16 g (0.05 mole) of the dried reaction product (2) of the one-pot process A are dissolved in 56.2 ml dimethylsulfoxide and added to a solution of 18.5 g (0.165 mole) sodium-tert.butylate in 67.2 ml dimethyl-sulfoxide within 5 minutes, while stirring with room temperature and keeping the system under nitrogen. The mixture is stirred for 10 minutes at 55° C., cooled down to 5° C. and mixed dropwise at the same temperature with 8 ml (0.1 mole) concentrated hydrochloric acid, which is diluted with 8 ml dimethyl-sulfoxide. Further 6.8 g (0.085 mole) 50% sodium hydroxide solution are added to the reaction mixture, which is then reacted with 10 ml (0.1 mole) dimethyl-sulfate and stirred for further 15 minutes. The reaction is then interrupted by adding 100 ml diluted ammonium-hydroxide solution and the reaction mixture is added to 500 ml diluted hydrochloric acid.

There are obtained 10.7 g 4-hydroxy-3-(5-methyl-3-isoxazolyl-carbamoyl)-2-methyl-2H-1,2-benzothiazin-1,1-dioxid (HPLC puritiy: 95%).

EXAMPLE 2

Manufacture of 4-Hydroxy-3-(2-pyridyl-carbamoyl)-2-methyl-2H-1,2-benzothiazin-1,1-dioxide

One-pot reaction A

A solution of 23.8 ml (0.3 mole) chloroacetylchloride in 60 ml ethylacetate is added dropwise during 15 minutes to a solution of 28.2 g (0.3 mole) 2-amino-pyridine in 750 ml ethyl-acetate at boiling temperature. The reaction mixture is left reacting for further 15 minutes. During the total reaction time there are 700 ml ethylacetate distilled off. A solution of 144 g (0.6 mole) sodium benzoic acid sulfimide dihydrate and 5 g (0.03 mole) potassium iodide in 434 ml dimethylformamide is then added to the reaction mixture. After 3.5 hours of further stirring, the mixture is poured on 3 liters of icewater and neutralized with diluted ammonium hydroxide solution. The product, which crystallises out is further isolated as described in Example 1. There are obtained 32.2 g (m.p. 178° C.).

One-pot reaction B

A solution of 6.34 g (0.02 mole) dried reaction product of reaction A in 19 ml dimethyl-formamide is added to a solution of 8.97 g (0.08 mole) potassium-tert.butylate in 27 ml dimethyl-formamide at room temperature and in an atmosphere of nitrogen. The reaction mixture is stirred for 60 minutes at 55° C. and for further 30 minutes at 80° C. The cooled down reaction product is partially neutralized at room temperature with 6 ml (0.04 mole) of semi-concentrated hydrochloric acid and during the course of 15 minutes reacted with 5 ml (0.05 mole) dimethyl-sulfate at 25° C. By adding 40 ml (0.04 mole) 1n-sodium-hydroxide solution while stirring the reaction is completed. The reaction mixture is finally stirred with 40 ml diluted ammonia solution, poured into 400 ml water and acidified with hydrochloric acid. There are obtained 2.5 g 4-hydroxy-3-(2-pyridyl-carbamoyl)-2-methyl-2H-1,2-benzothiazinl, 1-dioxide. The product is purified by recrystallisation from methanol or dichloromethane-methanol (7:3) (m.p. 199.5° C.).

EXAMPLE 3

Manufacture of 4-hydroxy-3-(2-thiazolyl-carbamoyl)-2-methyl-2H-1,2-benzothiazin-1,1-dioxid One-pot reaction A A solution of 40 ml (0.5 mole) chloroacetyl-chloride in 60 ml ethyl acetate is added dropwise to a boiling solution of 50.1 g (0.5 mole) 2-amino-thiazole in ethylacetate. The reaction mixture is then boiled under reflux and stirred for another period of 30 minutes, during which 800 ml ethyl acetate are distilled off. Subsequently, solution of 240 g (1 mole) sodium-benzoic acid dihydrate and 8.3 g (0.05 mole) potassium iodide in 434 ml dimethylformamide is added and the mixture is stirred for a period of 45 minutes at 90° C. The reaction mixture is then diluted with water and neutralized with 1n-aqueous ammonia solution. The precipitated product is isolated and washed first with isopropanol and then with petrolether and dried. There are obtained 116 g (m.p. 247.3° C.).

One-pot reaction B

A solution of 3.23 g (0.01 mole) dried product of reaction A in 9.7 ml dimethyl-formamide is added at roomm temperature to a stirred solution of 4.48 g (0.04 mole) potassium-tert.butylate in 13.5 ml dimethyl-formamide in an atmosphere of nitrogen. The reaction mixture is stirred for a period of 30 minutes at 55° C. and then cooled down and partly neutralized at room temperature with 3 ml semiconcentrated hydrochloric acid. The mixture is then reacted for a period of 30 minutes at 25° C. with 2 ml (0.02 mole) dimethyl-sulfate. The reaction mixture is then mixed with 20 ml diluted aqueous ammonia solution and poured under stirring into 100 ml diluted hydrochloric acid. There are obtained 1.7 g 4-hydroxy-3-(2-thiazolyl-carbamoyl)-2-methyl-2H-1,2benzothiazin-1,1-dioxide. The product is purified by recrystallisation from acetone (m.p. 236.8° C., decomposition).

We claim:

1. A process for the preparation of a compound of the formula

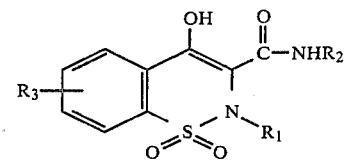

in which
$R_1$ is a hydrogen atom or a methyl radical, $R_2$ is thiazole, pyridine, or thiazole or pyridine substituted by methyl or methoxy and $R_3$ is a hydrogen or halogen atom or a methyl radical, or an alkali metal, alkaline earth metal or amine salt thereof, which comprises carrying out the following steps in one-pot A:
(i) reacting a corresponding thiazole or pyridine amine with a haloacetyl halide in boiling ethyl acetate, and
(ii) reacting the intermediate formed, without isolation, with sodium benzoic acid sulphimide to afford a compound of the formula

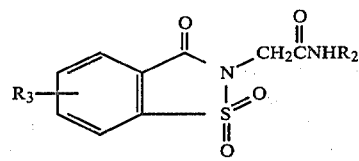

wherein
$R_3$ and $R_2$ are as defined above; carrying out the following steps in one-pot B:
(i) reacting the product from A with 3 to 4 equivalents of a strongly basic alkali-alcoholate in a dipolar aprotonic solvent under an atmosphere of a protection gas,
(ii) adding so much acid that about 2 equivalents of base remain and, if desired,
(iii) reacting the resulting product, without isolation, with dimethyl sulfate to provide a compound of the formula in which $R_1$ is methyl and, if further desired, converting the above product, without isolation, by known means to an alkali metal, alkaline earth metal or amine salt thereof.

2. A process according to claim 1, wherein the strongly basic alkali alcoholate is potassium tert-butylate.

3. A process according to claim 2, wherein the acid used is hydrochloric acid.

4. A process according to claim 1, wherein the reaction of the intermediate with sodium benzoic acid sulphimide is carried out in the presence of potassium iodide.

5. A process for the preparation of a compound of the formula

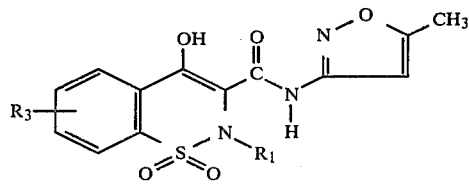

wherein $R_1$ is a hydrogen atom or methyl radical and $R_3$ is a hydrogen or halogen atom or a methyl radical, or an alkali metal, alkaline earth metal or amine salt thereof, which comprises carrying out the following steps in one-pot A:

(i) reacting 3-amino-5-methylisoxazole with a haloacetyl halide in boiling ethyl acetate, and (ii) reacting the intermediate formed, without isolation, with sodium benzoic acid sulphimide to afford a compound of the formula

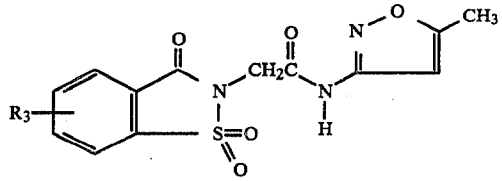

wherein $R_3$ is as defined above; carrying out the following steps in one-pot B:

(i) reacting the product from A with 3 to 4 equivalents of a strongly basic alkali-alcoholate in a dipolar aprotonic solvent under an atmosphere of a protection gas to afford a compound of the following formula which is not isolated

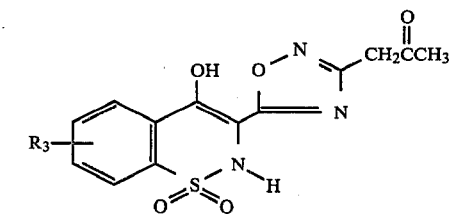

wherein $R_3$ is defined above, and (ii) adding so much acid that 2 equivalents of base remain to the above reaction to afford a compound of the formula

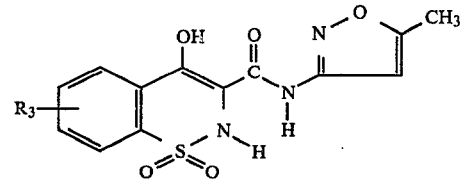

wherein $R_3$ is as defined above, and, if desired, (iii) reacting the above product, without isolation, with dimethylsulfate to provide a compound of the formula in which $R_1$ is methyl, and if further desired, converting the above product, without isolation, by known means to an alkali metal, alkaline earth metal or amine salt thereof.

6. A process according to claim 5, wherein the strongly basic alkali alcoholate is potassium tert-butylate.

7. A process according to claim 6, wherein the acid used is hydrochloric acid.

8. A process according to claim 5, wherein the acid addition step is carried out at a temperature of from $-5$ to 25° C.

9. A process according to claim 5, wherein the reaction of the intermediate with sodium benzoic acid sulphimide is carried out in the presence of potassium iodide.

* * * * *